US008884064B2

(12) United States Patent
Kuhnke et al.

(10) Patent No.: US 8,884,064 B2
(45) Date of Patent: Nov. 11, 2014

(54) METHOD OF SEPARATING OFF MAGNETIZABLE CATALYST PARTICLES BY MEANS OF MAGNETIC FILTERS

(75) Inventors: Frank Kuhnke, Ludwigshafen (DE); Jörg Heilek, Bammental (DE); Daniela Rieck, Alzey (DE)

(73) Assignee: BASF SE (DE)

( * ) Notice: Subject to any disclaimer, the term of this patent is extended or adjusted under 35 U.S.C. 154(b) by 193 days.

(21) Appl. No.: 13/339,523

(22) Filed: Dec. 29, 2011

(65) Prior Publication Data

US 2012/0172616 A1 Jul. 5, 2012

Related U.S. Application Data

(60) Provisional application No. 61/427,807, filed on Dec. 29, 2010.

(51) Int. Cl.
*C07C 209/48* (2006.01)
*C07C 209/84* (2006.01)

(52) U.S. Cl.
CPC ............. *C07C 209/84* (2013.01); *C07C 209/48* (2013.01)
USPC ........................................ 564/492

(58) Field of Classification Search
None
See application file for complete search history.

(56) References Cited

U.S. PATENT DOCUMENTS

| 4,605,678 A | 8/1986 | Brennan et al. |
| 2003/0023083 A1 | 1/2003 | Luyken et al. |
| 2009/0065437 A1 | 3/2009 | Mohedas |

FOREIGN PATENT DOCUMENTS

| CA | 2328391 | 6/2001 | |
| CN | 101 480 549 A | 7/2009 | |
| DE | 1081020 B | * 5/1960 | ............... B01J 25/02 |
| DE | 1081020 B | 5/1960 | |
| DE | 20 36 277 A1 | 1/1972 | |
| DE | 100 25 964 A1 | 12/2001 | |
| EP | 0014802 | 3/1984 | |
| GB | 1354 148 A | 6/1974 | |
| JP | 60 137439 A | 7/1985 | |
| WO | WO-2001066514 A1 | 9/2001 | |
| WO | WO-2008000808 A1 | 1/2008 | |

OTHER PUBLICATIONS

Whitesides, G.M., et al., "Magnetic Filtration of Small Heterogeneous Catalyst Particles. Preparation of Ferrimagnetic Catalyst Support", I & EC Process Design & Development, vol. 15, (1976), pp. 226-227.
International Search Report PCT/EP2011/074116 dated May 22, 2012.
International Preliminary Report on Patentability for PCT/EP2011/074116 Dated Jun. 12, 2012.
"Activated Base Metal Catalysts", EVONIK, 2009, http://catalysts.evonik.com/sites/dc/Downloadcenter/Evonik/Product/Catalysts/Brochures/3 25 Document.pdf.
"Filtration: Electromagnetic Filtration", Ultrapure Water, Jan./Feb. 1990, pp. 31-33.
"Handling Procedure for Degussa's Activated Base Metal Catalysts and Metalyste", Jul. 5, 2001.
Spevakova, "New magnetic Filter for Chemical Industry", Magnetic and Electrical Separation, vol. 5, pp. 17-32, 1993.
Hill, "High-Gradient Magnetic Filtration of Small Particles of Ferro-, Ferr-, and Paramagnetic Catalysts and Catalyst Support", Journal of Catalysts, vol. 43, p. 53-60, 1976.
"Handling Procedure for Activated Base Metal Catalysts and Metalystss", Degussa, May 24, 2004.

* cited by examiner

*Primary Examiner* — Brian J Davis
(74) *Attorney, Agent, or Firm* — Drinker Biddle & Reath LLP

(57) ABSTRACT

The present invention relates to a process comprising at least the steps (A) chemical reaction of at least one organic compound in the presence of at least one heterogeneous catalyst in a reaction mixture and (B) removal of the at least one heterogeneous catalyst by means of a magnetic filter, and also the use of a magnetic filter for separating off catalyst particles in a process for the hydrogenation of at least one organic compound.

11 Claims, 6 Drawing Sheets

US 8,884,064 B2

METHOD OF SEPARATING OFF MAGNETIZABLE CATALYST PARTICLES BY MEANS OF MAGNETIC FILTERS

CROSS-REFERENCE TO RELATED APPLICATIONS

This application claims the benefit of U.S. Provisional Application No. 61/427,807, filed Dec. 29, 2010, which is incorporated by reference.

BACKGROUND OF THE INVENTION

The present invention relates to a process comprising at least the steps (A) chemical reaction of at least one organic compound in the presence of at least one heterogeneous catalyst in a reaction mixture and (B) removal of the at least one heterogeneous catalyst by means of a magnetic filter, and also the use of a magnetic filter for separating off catalyst particles in a process for the hydrogenation at least one organic compound.

Methods of separating catalyst particles from reaction mixtures are already known from the prior art.

DE 1 081 20 discloses a process for the hydrogenation of adipodinitrile and epsilon-aminocapronitrile to form hexamethylenediamine by means of a suspended Raney catalyst under superatmospheric pressure. After reaction of the organic compounds mentioned, the catalyst-rich suspension can be freed of catalyst particles present in suspension by means of a cyclone or a magnetic separator.

CA 2,328,391 A1 discloses a method of separating off liquid constituents of a suspension. For this purpose, the suspension, which originates, for example, from chemical reactions such as dehydrogenations, hydrogenations, transhydrogenations, aromatizations, hydrodenitrations, is firstly treated by means of filtration, decantation, separation by means of a hydrocyclone, etc., and a magnetic separation is subsequently carried out.

WO 2008/000808 A1 discloses a process, for example a hydroformylation, carbonylation, olefin oligomerization and polymerization reactions, in which catalysts comprising cobalt, nickel or iron are used. After carrying out the chemical reaction, the solid catalyst components are separated off by means of magnetic filters.

The prior art has not previously described any processes which make it possible for the reaction mixture to be freed virtually entirely of solid catalyst particles in order to obtain particularly pure reaction mixtures. The processes of the prior art are therefore still in need of improvement in respect of the purity of the reaction mixtures obtained. For this purpose, it is necessary, in particular, to improve the step of removal of the suspended heterogeneous catalyst particles in order to obtain reaction mixtures which have a particularly high purity, so that in further work-up steps for the reaction mixture, for example in a work-up by distillation, disadvantages such as coating of the distillation columns with catalyst or blockage of the feed lines and/or discharge lines can be avoided.

BRIEF SUMMARY OF THE INVENTION

It is therefore an object of the present invention to provide a process for the reaction of organic compounds in the presence of a heterogeneous catalyst, which makes it possible to obtain the reaction mixture, i.e. the reaction output, in a particularly high purity, in particular free of residual catalyst particles. A further object is to provide a corresponding process which makes it possible to carry out steps following the process, in particular the work-up of the reaction mixture by distillation, in an advantageous manner. In particular, it is an object of the present invention to provide a corresponding process in which the distillation columns used in the work-up of the reaction mixture by distillation are not adversely affected by catalyst residues present in the reaction mixture, for example as a result of catalyst residues depositing in the distillation columns. A further object is to suppress the formation of undesirable by-products during the work-up of the product, for example during a distillation.

These objects are achieved according to the invention by a process comprising at least the steps:
  (A) chemical reaction of at least one organic compound in the presence of at least one heterogeneous catalyst in a reaction mixture and
  (B) removal of the at least one heterogeneous catalyst by means of a magnetic filter.

DETAILED DESCRIPTION OF THE INVENTION

Figure 1:
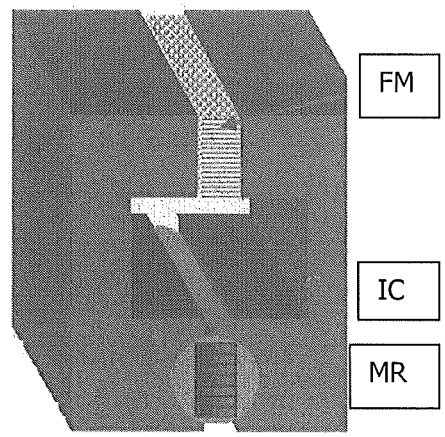
FIG. 1 shows the functional principle of a high-gradient magnetic filter which can be used according to the invention.
Figure 1:
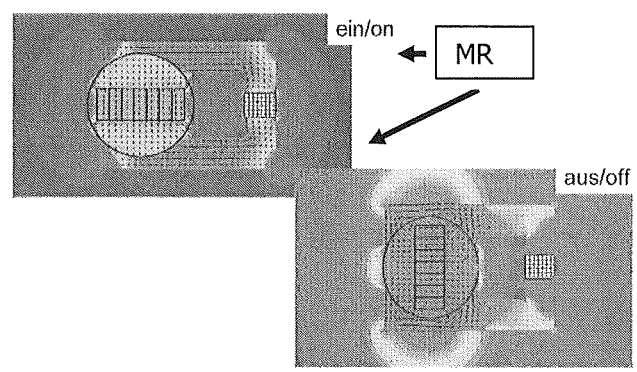

The process of the invention is explained in detail below.

Step (A):

Step (A) of the process of the invention comprises the chemical reaction of at least one organic compound in the presence of at least one heterogeneous catalyst in a reaction mixture.

In general, the process of the invention can be applied to any chemical reaction known to those skilled in the art in which a heterogeneous catalyst, in particular a ferromagnetic catalyst, is used.

Examples of chemical reactions which are particularly suitable for the purposes of the invention are selected from the group consisting of hydrogenations, dehydrogenations, isomerizations, aromatizations and combinations thereof.

In a particularly preferred embodiment, the chemical reaction carried out in step (A) of the process of the invention is a hydrogenation of organic compounds.

The present invention therefore provides, in particular, the process of the invention in which the chemical reaction is a hydrogenation.

The term "hydrogenation" is known per se to those skilled in the art and generally describes the reaction of C—C and/or C-heteroatom double or triple bonds comprised in organic compounds with a reducing agent, for example hydrogen in elemental or molecular form, in order to obtain the respective organic compounds in correspondingly reduced form.

According to the invention, all compounds known to those skilled in the art which appear to be suitable for a reaction in the presence of at least one heterogeneous catalyst can in principle be used as substrates, i.e. as starting compounds or starting materials, in step (A) of the process of the invention.

In Schritt (A) of the process of the invention, it is possible to use monomeric, low molecular weight organic compounds, for example compounds having 1 to 20 carbon atoms, preferably from 1 to 12 carbon atoms, particularly preferably from 1 to 8 carbon atoms, or polymeric organic compounds. If polymeric compounds are used in step (A) of the process of the invention, these have, for example, a molecular weight of from 500 to 100 000 g/mol.

When the chemical reaction in step (A) of the process of the invention is a hydrogenation of at least one organic compound, the at least one organic compound comprises, in particular, at least one functional group selected from the group consisting of C—C double bond, C—C triple bond, oxime group, imino group, nitrile group, carboxylic acid group, carboxylic ester group, carboxylic anhydride group, aldehyde group, keto group and mixtures thereof.

The present invention therefore provides, in particular, the process of the invention in which the chemical reaction in step (A) of the process of the invention is a hydrogenation of at least one organic compound, where the at least one organic compound used comprises at least one functional group selected from the group consisting of C—C double bond, C—C triple bond, oxime group, imino group, nitrile group, carboxylic acid group, carboxylic ester group, aldehyde group, keto group and mixtures thereof.

In step (A) of the process of the invention, it is possible to hydrogenate C—C doubles to C—C single bonds, C—C triple bonds to C—C double bonds and/or C—C single bonds. Furthermore, an oxime, imino or nitrile group can be hydrogenated to the corresponding amino group. A carboxylic acid, carboxylic ester, carboxylic anhydride, aldehyde or keto group can in each case be hydrogenated to the corresponding alcohol function in step (A) of the process of the invention.

In a particularly preferred embodiment, at least one organic compound having at least one nitrile group is hydrogenated in step (A) of the process of the invention. Organic compounds which have at least one nitrile group and are particularly suitable for the purposes of the invention are, for example, selected from the group consisting of mononitriles, dinitriles and polynitriles. These particularly preferred compounds are preferably hydrogenated to the corresponding amines in step (A). Corresponding compounds which have more than one nitrile group, for example two nitrile groups, can also be hydrogenated only partially according to the invention. For example, dinitriles can be hydrogenated to aminonitriles.

Particularly preferred organic compounds which are hydrogenated in step (A) of the process of the invention are selected from the group consisting of acetonitrile, propionitrile, 3-dimethylaminopropionitrile, i-phoronenitrile, adipodinitrile and mixtures thereof. These compounds are preferably hydrogenated to the corresponding amines; for example, it is possible to hydrogenate acetonitrile to ethylamine, propionitrile to n-propylamine, 3-dimethylaminopropionitrile to 3-dimethylaminopropylamine and i-phoronenitrile to i-phoronediamine.

The present invention therefore particularly preferably provides the process of the invention in which the at least one organic compound which is hydrogenated in step (A) of the process of the invention is selected from the group consisting of acetonitrile, propionitrile, 3-dimethylaminopropionitrile, i-phoronenitrile, adipodinitrile and mixtures thereof.

Particular preference is given to hydrogenating adiponitrile (ADN) to hexamethylenediamine (HMD) or 6-aminocapronitrile (6-ACN) and hexamethylenediamine (HMD) in step (A) of the process of the invention.

The present invention therefore preferably provides the process of the invention in which adiponitrile (ADN) is hydrogenated to hexamethylenediamine (HMD) or 6-aminocapronitrile (6-ACN) and hexamethylenediamine (HMD) in step (A).

Processes for hydrogenating adipodinitrile are known per se to those skilled in the art and are described, for example, in H. J. Arpe, Industrielle organische Chemie, 6th edition, p. 275, Wiley-VCH-Verlag.

Hexamethylenediamine (HMD) is an important monomer, for example for the preparation of polyamides. Polyamide-6.6 ("Nylon") can be prepared from adipic acid and hexamethylenediamine by polycondensation. Reaction of hexamethylenediamine with phosgene gives the diisocyanate which can serve as component for the production of polyurethane resins and polyurethane foams.

In a preferred embodiment of the invention, hexamethylenediamine can therefore be prepared by catalytic liquid-phase hydrogenation of adiponitrile in the presence of iron, cobalt or nickel catalysts in step (A) of the process of the invention.

In a preferred embodiment of step (A) of the process of the invention, adiponitrile is converted into hexamethylenediamine in a high-pressure process, for example at a temperature of from 100 to 200° C., a pressure of from 200 to 400 bar, in the presence of ammonia as solvent and an iron-comprising fixed-bed catalyst.

In a further preferred embodiment of step (A) of the process of the invention, adiponitrile is converted into hexamethylenediamine in a low-pressure suspension process. This process is carried out, for example, at from 60 to 100° C. and at, for example, 20 to 50 bar (pressure), preferably in the presence of alkali metal-modified Raney nickel and hexamethylenediamine as solvent.

In the hydrogenation of organic compounds which is preferably carried out according to the invention, it is generally possible to use any suitable reducing agent. Hydrogen is preferably used as reducing agent in step (A) of the process of the invention.

Both preferred embodiments of step (A) of the process of the invention result in formation of hexamethylenediamine, for example with selectivity of 99% at a conversion of, for example, 99%. The hydrogenation of adiponitrile to hexamethylenediamine is strongly exothermic, see also Winnacker/Küchler, Chemische Technik, volume 5, Organische Zwischenverbindungen, Polymere, 5th edition, Wiley-VCH-Verlag 2005, pages 242 and 244, and also FIG. 9.2 on page 243. See also FIG. 2.

In step (A) of the process of the invention, a chemical reaction is carried out in the presence of at least one heterogeneous catalyst.

In general, all heterogeneous catalysts known to those skilled in the art can be used in the process of the invention. The at least one heterogeneous catalyst according to the invention is, according to the invention, preferably ferromagnetic, in order to make a magnetic separation possible in step (B). The at least one heterogeneous catalyst is particularly preferably present in emulsified or suspended form.

For example, the heterogeneous catalysts can comprise catalytically active metals selected from the group consisting of nickel, cobalt, iron and mixtures thereof.

The present invention therefore provides, in particular, the process of the invention in which the at least one heterogeneous catalyst comprises a metal selected from the group consisting of Ni, Fe, Co and mixtures thereof.

The catalytically active metals, in particular the metals stated to be preferred, can be present in elemental form. If the heterogeneous catalyst is present in elemental form, it is preferably present in the form of particles, for example particles having a particle size distribution of from 0.1 to 5000 µm, preferably from 1 to 1000 µm, particularly preferably from 1 to 100 µm. According to the present invention these size ranges also apply to agglomerates which are optionally formed from the particles in an additional step, i.e. although the particle size increases by agglomeration, the size of the obtained agglomerates is still in the mentioned range. In a further preferred embodiment, these particles which are preferably present are suspended in the reaction mixture of step (A) of the process of the invention.

For example, the heterogeneous catalysts can be present in the form of the Raney metal. This embodiment of a heterogeneous catalyst is known per se to those skilled in the art. In particular, nickel is present in the form of Raney nickel, cobalt is present in the form of Raney cobalt and iron is present in the form of Raney iron, see, for example, Römpp Chemie Lexikon, 9th edition, volume 5, page 3785, column 2, Georg Thieme Verlag Stuttgart, N.Y.

In a preferred embodiment of step (A) of the process of the invention, nickel is present in the form of Raney nickel and/or cobalt is present in the form of Raney cobalt as heterogeneous catalyst.

In a further preferred embodiment of the process of the invention, the heterogeneous catalyst is present as a fixed bed in the reaction mixture. A catalyst support is preferably not present here. The catalyst precursor comprises, for example, iron oxides, cobalt oxides and/or nickel oxides which are reduced to the corresponding metals before the chemical reaction in step (A). This is preferably affected by reduction by means of hydrogen.

In this embodiment, the heterogeneous catalyst is preferably present in a fixed arrangement in the reactor in which the chemical reaction of step (A) of the process of the invention is carried out. In addition, part of the heterogeneous catalyst can also be suspended in the reaction mixture in this embodiment.

The heterogeneous catalysts present in the process of the invention are, in a further preferred embodiment, applied to an appropriate support material, for example metal oxides and/or semimetal oxides, zeolites, activated carbons, ceramics, etc., and suspended or arranged as a fixed bed in the reaction mixture, in particular in a liquid reaction medium. The catalytically active metals are preferably present in metallic form on the support material.

The at least one heterogeneous catalyst present according to the present invention generally has a particle size distribution of from 0.1 to 5000 µm, preferably from 1 to 1000 µm, particularly preferably from 1 to 100 µm. According to the present invention the size ranges apply to particles as well as to agglomerates that are optionally formed.

The present invention therefore preferably relates to the process according to the present invention, wherein the at least one heterogeneous catalyst has a particle size distribution of 0.1 to 5,000 µm, preferably 1 to 1,000 µm, particularly preferably 1 to 100 µm.

Step (A) of the process of the invention comprises a chemical reaction which takes place in a reaction mixture. The reaction mixture is formed here at least by the organic compounds to be reacted in the chemical reaction, optionally further reagents, for example in liquid, solid, dissolved, suspended or gaseous form, the at least one heterogeneous catalyst and products formed during the chemical reaction. In one possible embodiment of step (A) of the process of the invention, the reaction mixture additionally comprises at least one solvent. The solvent can in principle be selected from among all solvents known to those skilled in the art, for example inorganic solvents, for example water or liquid ammonia, or organic solvents, for example alcohols, open-chain and cyclic ethers, alkanes and mixtures thereof.

In the hydrogenation of adiponitrile to hexamethylenediamine or 6-aminocapronitrile and hexamethylenediamine which is preferably, according to the invention, carried out in step (A) of the process of the invention, preference is given to using no solvent. If a solvent is nevertheless added, it can be selected from among the abovementioned solvents.

Step (A) of the process of the invention is, for example, carried out continuously or batchwise, preferably continuously.

In the reaction mixture of step (A) of the process of the invention, the at least one heterogeneous catalyst is generally present in an amount which is known to be suitable to those skilled in the art, for example from 1 to 50% by weight, preferably from 2 to 40% by weight, particularly preferably from 5 to 30% by weight, in each case based on the total reaction mixture.

In a preferred embodiment of the process of the invention, part of the at least one heterogeneous catalyst is separated off after step (A) and before step (B) according to the invention.

The present invention therefore preferably provides the process of the invention in which part of the at least one heterogeneous catalyst is separated off before step (B).

When fixed-bed catalysts are used, this removal is preferably omitted. Any abraded catalyst material formed is, according to the invention, preferably removed by means of a magnetic filter, preferably with a back-flushable magnetic filter, for example a high gradient-magnetic filter or an automag magnetic filter, or a wet drum separator.

For the purposes of the present invention, "part" means, for example, from 80 to 99.99% by weight of the total amount of at least one heterogeneous catalyst present, preferably from 90 to 99.99% by weight, particularly preferably from 95 to 99.99% by weight.

This first separation step which is preferably carried out according to the invention in the present process is, for example, carried out in order to separate off a major part of the at least one heterogeneous catalyst after step (A) and before step (B).

If a fixed-bed catalyst is used in step (A) of the process of the invention, this additional removal after step (A) and before step (B) is, according to the invention, preferably not carried out. If a heterogeneous catalyst in suspension is used in step (A) of the process of the invention, this additional removal after step (A) and before step (B) is, according to the invention, preferably carried out.

The removal of part of the at least one heterogeneous catalyst can in principle be carried out by all methods known to those skilled in the art.

In a preferred embodiment of the process of the invention, the removal before step (B) is effected by filtration, for example by means of candle filters, filter presses, backflush filters, belt filters, drum filters, rotary pressure filters, etc., by crossflow filtration, for example by means of Dyno Filters, and MSD separator, wound membrane module, hollow fiber module, etc., by separation in the earth's gravitational field, for example by means of clarification vessels/settling vessels, lamellar clarifiers, etc., by separation in a centrifugal field, for example by means of a plate separator, hydrocyclone, decanter centrifuge, solid wall screw centrifuge, sieve decanter, peeler centrifuge, invertible filter centrifuge, gyratory centrifuge, pusher centrifuge, etc., by sieving, for example by means of a vibratory sieve, vibratory chute, arc sieve, etc., or combinations thereof.

The present invention therefore preferably provides the process of the invention in which the removal before step (B)

is carried out by filtration, by crossflow filtration, by separation in the earth's gravitational field, by separation in a centrifugal field, by sieving or a combination thereof.

Furthermore, the present invention preferably provides the process of the invention in which the removal before step (B) is carried out by means of a hydrocyclone, at least one settling vessel, at least one clarification vessel and/or at least one plate separator.

Furthermore, the present invention preferably provides the process of the invention in which the removal before step (B) is carried out using a clarification vessel/settling vessel.

Furthermore, the present invention preferably provides the process of the invention in which the removal before step (B) is carried out using a clarification vessel/settling vessel and a hydrocyclone.

A combination of clarification vessel/settling vessel and hydrocyclone is preferably used according to the invention. Furthermore, the reaction mixture can be treated by means of steps which are known per se to those skilled in the art; for example, gaseous components of the reaction mixture can be separated off by lowering the pressure.

In a preferred embodiment, the reaction mixture which is obtained after the chemical reaction taking place in step (A) of the process of the invention and comprising, for example, the organic compound to be reacted in the chemical reaction, optionally further reagents, for example in liquid, solid, dissolved, suspended or gaseous form, the at least one heterogeneous catalyst and products formed during the chemical reaction, optionally in an appropriate solvent, is freed of part of the catalyst by means of at least one clarification vessel, i.e. settling vessel, preferably one clarification vessel, and a first hydrocyclone.

For the purposes of the present invention, the formulation "a first hydrocyclone" refers either to a single first hydrocyclone or preferably to a formation of hydrocyclones operated in parallel, for example at least two hydrocyclones, preferably, for example, five hydrocyclones. A plurality of hydrocyclones operated in parallel are used, for example, depending on the reaction mixture to be treated. For example, a hydrocyclone stage made up of five hydrocyclones operated in parallel is used for a capacity of 120 kt/a. In all separation apparatuses mentioned in the context of the present invention, a plurality of identical apparatuses can, according to the invention, be connected in parallel in order to be able to treat the appropriate amount of reaction mixture.

Hydrocyclones are known per se to those skilled in the art and are described, for example, in Rompp Chemie Lexikon, 9th expanded and revised edition, 1990, page 1912, G. Thieme Verlag Stuttgart N.Y.

According to the invention, the reaction mixture obtained from step (A) is preferably firstly conveyed through at least one clarification vessel in order to separate off part of the at least one heterogeneous catalyst suspended in the reaction mixture. In a preferred embodiment, at least one clarification vessel is used first, then at least one first hydrocyclone. An overflow stream from the first hydrocyclone which, according to the invention, preferably has a low content of at least one heterogeneous catalyst of from 5 to 10 000 ppm by weight, particularly preferably from 10 to 1000 ppm by weight, very particularly preferably from about 20 to 500 ppm by weight, in each case based on the reaction mixture obtained at the overflow of the first hydrocyclone, is obtained. This stream is preferably fed to step (B), i.e. the remaining at least one heterogeneous catalyst is separated off by means of a magnetic filter. Furthermore, a bottom outlet stream which comprises part of the at least one heterogeneous catalyst which is separated off in this separation step which is preferred according to the invention is obtained. To discharge or recover the at least one heterogeneous catalyst and preferably recirculate it to step (A) of the process of the invention, this bottom outlet stream is, according to the invention, preferably fed to at least one second hydrocyclone. Here, a second overflow stream which can, for example, comprise solvents, starting material and/or product is obtained. Furthermore, a second bottom outlet stream which comprises a major part of at least one heterogeneous catalyst is obtained. This can, optionally after work-up, be reused in step (A) of the process of the invention. Furthermore, the overflow stream of the second hydrocyclone is preferably fed to the inlet of the first hydrocyclone in order to be able to feed more product to the subsequent distillation stage.

In a preferred embodiment, the residual amount of the at least one heterogeneous catalyst, in particular the iron, cobalt and nickel catalyst, remaining after the preferred removal according to the invention of part of the at least one heterogeneous catalyst is present in particulate form dispersed in the reaction mixture.

In a preferred embodiment, this reaction mixture optionally comprises solvent, which can also be separated off in a further step, and predominantly the desired product of the chemical reaction carried out in step (A), particularly preferably the desired hydrogenation product. The reaction mixture can, after the preferred removal of part of the at least one heterogeneous catalyst, also comprise as yet unreacted starting materials or intermediates and/or from 0.1 to 50% by weight of water, preferably from 0.5 to 40% by weight, particularly preferably from 1 to 30% by weight, of water, in each case based on the total reaction mixture.

In a preferred embodiment of the process of the invention, this reaction mixture from which part of the at least one heterogeneous catalyst and optionally solvent has preferably been separated off is transferred directly to step (B) of the process of the invention. In the use which is preferred according to the invention of a clarification vessel or a clarification vessel and a hydrocyclone, this stream which is transferred to step (B) of the process of the invention preferably corresponds to the overflow stream from the clarification vessel or the overflow stream from the first hydrocyclone.

After the preferred removal of part of the at least one heterogeneous catalyst from the reaction mixture before step (B) of the process of the invention, the content of at least one heterogeneous catalyst in the reaction mixture which is used in step (B) of the process of the invention is preferably from 5 to 10 000 ppm by weight, particularly preferably from 10 to 1000 ppm by weight, very particularly preferably from about 20 to 500 ppm by weight, in each case based on the reaction mixture to be treated.

The at least one heterogeneous catalyst that is present in the reaction mixture according to step (A) is in a further preferred embodiment agglomerated.

In a further preferred embodiment, the at least one heterogeneous catalyst that is present in the reaction mixture according to step (A) is agglomerated after separation of the part of the at least one heterogeneous catalyst from the reaction mixture.

Therefore, the present invention preferably relates to the process according to the present invention, wherein the at least one heterogeneous catalyst that is present in the reaction mixture according to, preferably after, step (A), preferably after separation of a part of the least one heterogeneous catalyst from the reaction mixture, is agglomerated.

According to the present invention, agglomeration means that small parts, i.e. the particles of the heterogeneous catalysts, accumulate to bigger particles, i.e. agglomerates, based on their attractive interactions.

In a particularly preferred embodiment, the agglomeration of the at least one heterogeneous catalyst that is present in the reaction mixture according to step (A) according to the present invention, takes place after step (A), i.e. after completion of the chemical reaction that is conducted in step (A). In a further preferred embodiment of the process according to the present invention, the agglomeration of the at least one heterogeneous catalyst that is present in the reaction mixture according to step (A) according to the present invention takes place before step (B).

Due to the preferably conducted agglomeration of catalyst particles to bigger agglomerates according to the present invention, the separability of the at least one heterogeneous catalyst from the reaction mixture can further be improved, wherein the rate of separation in step (B) of the process according to the present invention can further be increased. A further advantage of the optional agglomeration of the catalyst particles according to the present invention is that for separation of the formed agglomerates magnetic filters, for example back-flushable magnetic filters, in particular automag magnetic filters, that are shaped in an easier way and that are therefore more cost effective, can be used in step (B) of the process according to the present invention.

The agglomeration of catalyst particles, which are present in the reaction mixture according to step (A) of the process according to the present invention, can in general be conducted by any processes that are known to the skilled artisan.

For example, according to the present invention, the agglomeration of catalyst particles can be obtained by slow stirring of the reaction mixture comprising the catalyst particles from step (A), in order to let the single particles get into contact with each other and agglomerate.

According to the present invention, the wording "slow stirring" means that during stirring the input of power is for example 0.05 to 0.5 kW/m$^3$ and/or the speed at the tip of the outmost stirrer perimeter (tip-speed) is 0.1 to 1 m/s.

The agglomeration of catalyst particles that is optionally conducted according to the present invention can for example be done using a panel stirrer (Scheibenrührer) that is known to the skilled artisan, which is preferably provided in an adequate distance to the bottom of the container. According to the present invention an "adequate distance" means for example that already agglomerated particles can settle at the bottom, without being dispersed again, for example the distance between panel stirrer (Scheibenrührer) and bottom is 1 m.

In a further preferred embodiment flow breakers that are known to the skilled artisan are provided in an adequate distance to the bottom of the container and/or the bottom of the container comprises a cone-shaped form.

In a further preferred embodiment of the present invention, stirring for agglomeration of the particles is conducted in a container having a cone-shaped double bottom. In this embodiment according to the present invention, a second cone-shaped bottom is provided in a distance to the bottom in the container, wherein stirring is only conducted in the space above the second bottom. Agglomerates that are preferably obtained in the upper space, settle down and get into the space between first and second bottom through a correspondingly provided hole. The size of the hole can be adjusted by the skilled artisan and depends preferably on the amount of the reaction mixture that is stirred, on the amount of catalyst particles that are to be agglomerated and on the size of the obtained agglomerates. For example, the diameter of the hole that is present in the second bottom is 0.02 to 0.3 m.

In a further preferred embodiment of the present invention agglomeration of catalyst particles can be obtained by addition of at least one flocculant to the reaction mixture of step (A). Examples of flocculants that are known to the skilled artisan are for example Sedipur®-products. Depending on the composition of the flocculant, it can be either anionic, cationic or non-ionic. Examples of anionic flocculants are anionic, substituted polyacrylamides with low and high molecular masses. Examples for non-ionic flocculants are non-ionic polyacrylamides. Examples of cationic flocculants are cationic, substituted polyacrylamides, polyethyleneimines, polyamines or polyDADMAC (polydiallyldimethylammonium chloride). The at least one flocculant is added in an amount that is known to the skilled artisan, for example 10 to 5,000 weight ppm, preferably 50 to 1,000 weight ppm, particularly preferably 50 to 200 weight ppm, in each case in relation to the product of the chemical reaction of at least one organic compound in step (A) of the process according to the present invention, for example hexamethylenediamine (HMD). For example, the optionally used at least one flocculant is used as 1% solution, preferably in water. At least one flocculant can be used for agglomeration in this case, wherein the product that is obtained in step (A) or the process according to the present invention itself is not disturbed.

The present invention therefore further relates to the process according to the present invention, wherein agglomeration of the catalyst particles is obtained by slow stirring of the reaction mixture from step (A) comprising catalyst particles and/or addition of at least one flocculant.

Step (B):

Step (B) of the process of the invention comprises removal of the at least one heterogeneous catalyst by means of a magnetic filter, preferably a back-flushable magnetic filter, for example a high gradient magnetic filter or an automag magnetic filter, or a wet drum separator is used.

Step (B) of the process of the invention is carried out in order to obtain a reaction mixture which has a particularly low residual content of at least one heterogeneous catalyst. The preferred use according to the invention of a back flushable magnet filter, for example a high-gradient magnetic filter or an automag magnetic filter or a wet drum separator makes it possible to obtain a reaction mixture having a particularly low residual content of at least one heterogeneous catalyst after step (B).

In a preferred embodiment, the content of at least one heterogeneous catalyst in the reaction mixture which is used in step (B) of the process of the invention is preferably from 5 to 10 000 ppm by weight, particularly preferably from 10 to 1000 ppm by weight, very particularly preferably from about 20 to 500 ppm by weight, in each case based on the reaction mixture to be treated.

The present invention therefore preferably provides the process of the invention in which the content of at least one heterogeneous catalyst in the reaction mixture which is used in step (B) of the process of the invention is preferably from 5 to 10 000 ppm by weight, particularly preferably from 10 to 1000 ppm by weight, very particularly preferably from about 20 to 500 ppm by weight, in each case based on the reaction mixture to be treated.

The at least one heterogeneous catalyst to be separated off according to the invention usually has a particle size distribution of from 0.1 to 5000 μm, preferably from about 0.1 to 1000 μm, particularly preferably from about 0.1 to 100 μm.

The separation in step (B) of the process of the invention is preferably carried out at a temperature of from 0 to 200° C., preferably from 20 to 100° C. The separation in step (B) of the process of the invention is preferably carried out at a pressure of from 0.2 to 200 bar (absolute), particularly preferably from 0.4 to 50 bar (absolute), very particularly preferably from 1 to 10 bar (absolute).

The separation in step (B) of the process of the invention is carried out continuously or batchwise, preferably continuously. In the case of continuous operation, the volume flow of the reaction output to be filtered is generally from 0.2 to 10 000 m$^3$/h, preferably from 3 to 1000 m$^3$/h and particularly preferably from 5 to 100 m$^3$/h.

The viscosity of the reaction mixture treated in step (B) is generally from 0.05 to 50 mPa*s, preferably from 0.6 to 5 mPa*s, in particular from 0.8 to 2 mPa*s.

The removal of the at least one heterogeneous catalyst is carried out in step (B) of the process of the invention using a magnetic filter. Preferably a back-flushable magnetic filter, for example a high gradient magnetic filter or an automag magnetic filter, or a wet drum separator is used.

The present invention therefore preferably relates to the process according to the present invention, wherein the magnetic filter is a back-flushable magnetic filter, for example a high-gradient-magnetic filter or an automag magnetic filter, or a wet drum separator.

Back flushable magnetic filters, for example high-gradient magnetic filters or automag magnetic filters, are known per se to those skilled in the art. These are "switchable" permanent magnet filters whose action is based on the deposition of magnetizable particles in highly homogeneous magnetic fields.

In the switched-on state, the permanent magnets are preferably aligned so that they generate the magnetic flux to the filter chamber by means of an iron yoke. The magnetic flux density of the filter at a pole spacing of, for example, 25 mm is, for example, about 0.3 T. In this position, separation of the iron-comprising particles from the liquid flowing through occurs. The particles are transported in the magnetic field to ferromagnetic collectors, for example fine wires of the material X6Cr17, which can also be referred to as filter matrix, and accumulated there, see also FIG. 1.

When a limiting loading of the filter matrix is reached, i.e. in the case of a no longer operable pressure drop over the filter matrix or unsatisfactory separation of magnetizable particles from the suspension to be filtered, the magnetic field is briefly switched off by rotating the permanent magnet and the filter matrix is cleaned by means of a flushing pulse. This back-flushing pulse should preferably be in the direction opposite to the flow direction of the filtrate, using organic components or water, but can also be in the flow direction of the filtration using water, organic components or filtrate. The backflushing pulse can, for example, be generated by means of a pump or from a vessel under superatmospheric pressure, for example blanketed with a gas cushion.

The magnetic action can alternatively be produced by means of electromagnets which are switched to the no-current state during the above-described backflushing. High-gradient magnetic filters which are suitable for the purposes of the invention can be obtained, for example, from Steinert.

Wet drum separators are also known per se to those skilled in the art. Here, the liquid preferably flows through a semicircular separation space under a stainless steel drum to which the magnetizable particles become attached. The strong, high-gradient magnetic field is, for example, generated by means of a cylinder comprising permanently magnetic disks within the drum. The special permanent magnets generate particularly high field gradients. When the drum is rotated, the filtercake is preferably moved upward from the suspension and out from the magnetic field. Despite the strong magnetic field in the separation space, the filtercake can easily be discharged since the cylinder with the permanent magnets is preferably arranged concentrically in the rotating drum. As a result, the magnetic field in the separation space is strong and that in the cake offtake zone is very weak. Wet drum separators which are suitable for the purposes of the invention can be obtained, for example, from Steinert.

Further preferred examples of back-flushable magnetic filters are automag magnetic filters, in particular automag skid AM6/SKID1 or AM12/SKID1, of Eclipse Magnetics Ltd.

In a preferred embodiment according to the present invention, beside the mentioned magnetic filters, can, in the case that the at least one heterogeneous catalyst that is present in the reaction mixture according to step (A), is agglomerated, preferably before step (B) according to the present invention is conducted, even simpler designed and therefore more cost effective magnetic filters be used, that are known to the skilled artisan, for example back flushable magnetic filters like Automag skid AM6/SKID1 or AM12/SKID1 of Eclipse Magnetics LTD.

After the step (B) according to the invention of the process of the invention, a reaction mixture which comprises the at least one heterogeneous catalyst in a particularly low concentration, for example from 0.1 to 100 ppm by weight, preferably from 0.1 to 20 ppm by weight, particularly preferably from 0.1 to 5 ppm by weight, is obtained.

This particularly low content according to the invention of at least one heterogeneous catalyst makes it possible to carry out a work-up step, for example a distillation of the reaction mixture obtained after step (B), particularly advantageously. Firstly, deposition of the at least one heterogeneous catalyst or degradation products thereof in the distillation columns is avoided. As a result, cleaning of the distillation column and an associated downtime of the plant are avoided. Furthermore, the formation of undesirable by-products formed from the desired product by reactions in the presence of the at least one heterogeneous catalyst or degradation products thereof during the distillation is suppressed, so that the desired product can be obtained in higher yield and purity.

Furthermore, the combination which is preferred according to the invention of a first removal of part of the at least one heterogeneous catalyst, for example by means of a clarification vessel and/or a hydrocyclone, in combination with step (B), viz. removal of the at least one heterogeneous catalyst using a magnetic filter, provides a process which consumes particularly little energy compared to known processes of the prior art. In addition, with the process according to the present invention, lower investment costs apply.

In a preferred embodiment of the process of the invention, step (B) is followed by the step (C) below:

(C) work-up of the reaction mixture from step (B), preferably by distillation, in order to obtain the desired product of the chemical reaction in step (A).

Processes for working up reaction mixtures are known per se to those skilled in the art. Furthermore, processes for distilling reaction mixtures are known per se to those skilled in the art and are described, for example, in Winnacker Küchler, Chemische Technologie, 4$^{th}$ edition, 1984, pages 180-199, Carl-Hanser Verlag, Munich, Vienna.

Figure 3:
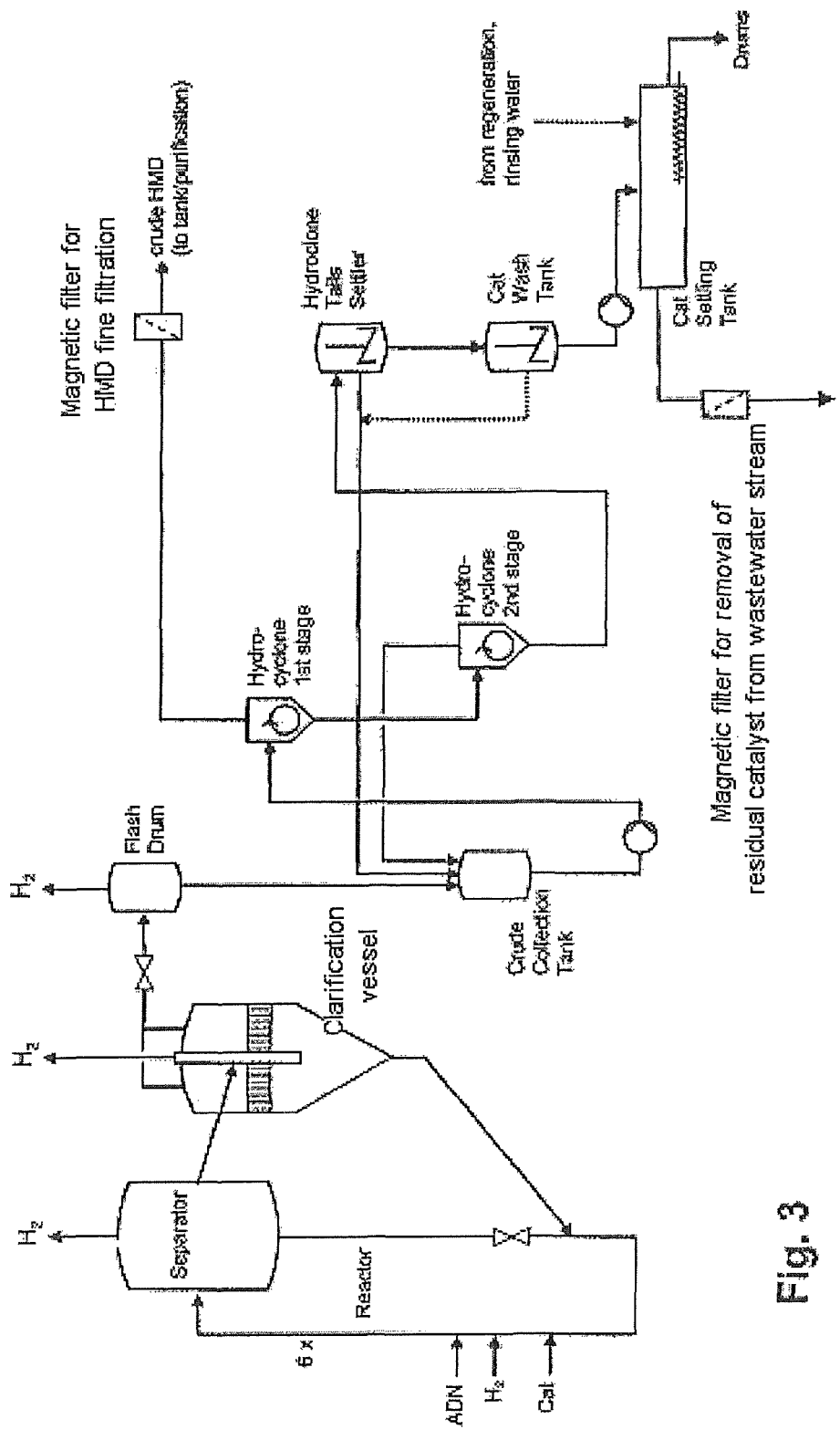
FIG. 3 shows a process scheme for the preparation of HMD from AND with subsequent catalyst removal.

A particularly preferred embodiment of the process of the invention is described below, see also FIG. 3.

A catalyst suspension comprising from 5 to 30% by weight of Raney nickel is obtained from the hydrogenation of adipodinitrile (ADN) by means of hydrogen to hexamethylenediamine (HMD) or 6-aminocapronitrile (6-ACN) and hexamethylenediamine (HMD). This suspension is firstly fed to a gas separation vessel from which a suspension stream runs into a clarification vessel. The lower outlet of the clarification vessel goes back to the reactor. The clarified upper offtake stream corresponding to from about 5 to 20% of the feed still comprises from 10 to 1000 ppm by weight of catalyst. The overflow stream is depressurized from reactor pressure level to a slightly superatmospheric pressure via a throttle valve. The gas liberated here is separated off in a separator. The liquid runs into a buffer vessel and from there is fed to a two-stage hydrocyclone battery.

First Hydrocyclone

The overflow stream from the first hydrocyclone stage has a residual content of from 10 to 1000 ppm by weight of Raney nickel and goes into the "crude HMD tank" and subsequently goes, after the removal according to the invention of Raney nickel by means of a high-gradient magnetic filter, into the first distillation column of the HMD work-up. According to the invention, the overflow stream from the first hydrocyclone stage is conveyed to the first work-up column. The nickel content of this stream can, according to the invention, be reduced to less than 5 ppm by weight.

Second Hydrocyclone

The bottom outlet stream from the first hydrocyclone stage is fed to the second hydrocyclone stage whose overflow stream goes back into the buffer vessel. The bottom outlet stream from the second stage, which is enriched in catalyst, goes into a settling vessel and from there to catalyst discharge.

The catalyst sediment accumulating in the catalyst discharge vessel ("hydrocyclone tails settler") is periodically drained into a second stirred vessel in which the catalyst is freed of HMD in a multistage batch process and is resuspended in water. The used catalyst is discharged via a settling tank from which the catalyst is dispensed while moist with water by means of a discharge screw into drums and passed to recycling. The supernatant aqueous liquid is preferably, according to the invention, likewise conveyed via a magnetic filter. Here too, the nickel content of the supernatant liquid can be reduced to less than 5 ppm.

The present invention also provides for the use of a magnetic filter, preferably of a back-flushable magnetic filter, for example a high-gradient magnetic filter or an automag magnetic filter, or a wet drum separator, for separation of catalyst particles in a process for the hydrogenation of at least one organic compound.

The present invention preferably provides the use according to the invention in which adiponitrile (ADN) is hydrogenated to hexamethylenediamine (HMD) or 6-aminocapronitrile (6-ACN) and hexamethylenediamine (HMD) in the process.

As regards the magnetic filter, the wet drum separator, the catalysts used, the process for the hydrogenation of at least one organic compound and also further details and preferred embodiments, what has been said in respect of the process of the invention, applies.

FIGURES

Figure 2:
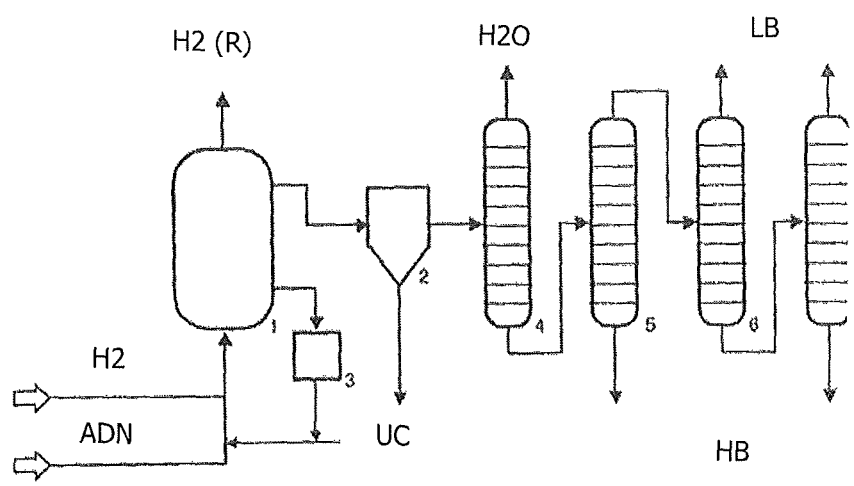
FIG. 2 shows a process scheme for the preparation of HMD from adiponitrile, without the separation process according to the invention.

FIG. 1 shows the functional principle of a high-gradient magnetic filter which can be used according to the invention. In FIG. 1, the abbreviations have the following meanings:
FM Filter matrix
IC Iron circle
MR Magnetic rotor FIG. 2 shows a process scheme for the preparation of HMD from adiponitrile, without the separation process according to the invention. In FIG. 2, the abbreviations have the following meanings:
H2 Hydrogen
ADN Adipodinitrile
H2 (R) Hydrogen for recirculation
LB Low boilers
HB High boilers
UC Used catalyst FIG. 3 shows a process scheme for the preparation of HMD from ADN with subsequent catalyst removal.

Figure 4:
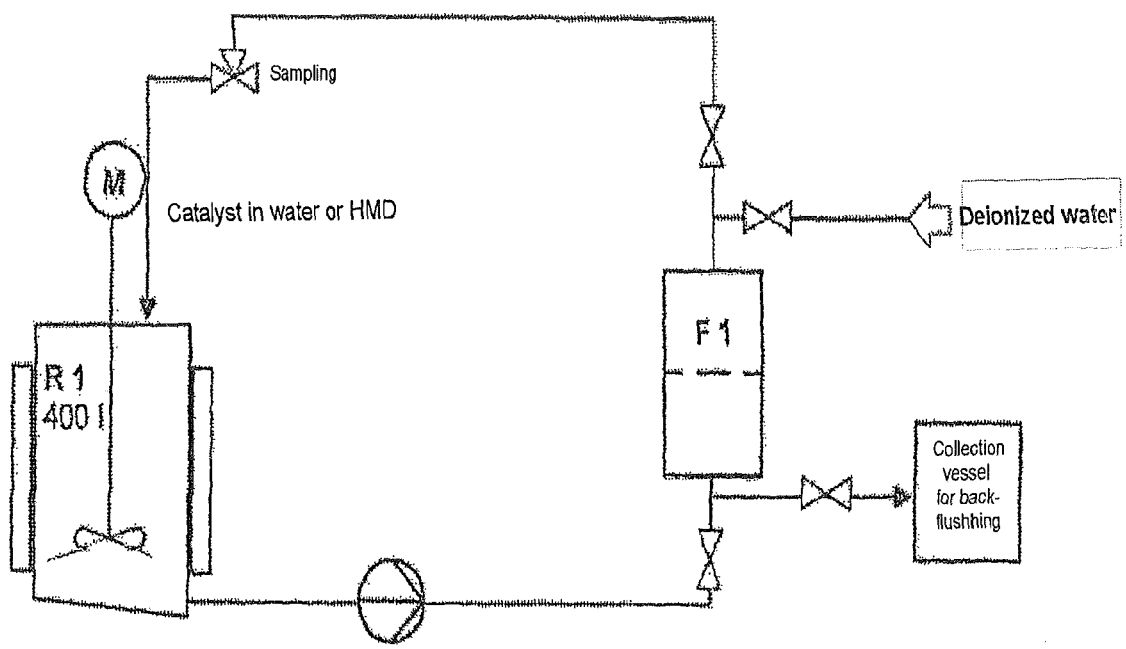
FIG. 4 schematically shows the experimental set-up used in the examples.
Figure 5:
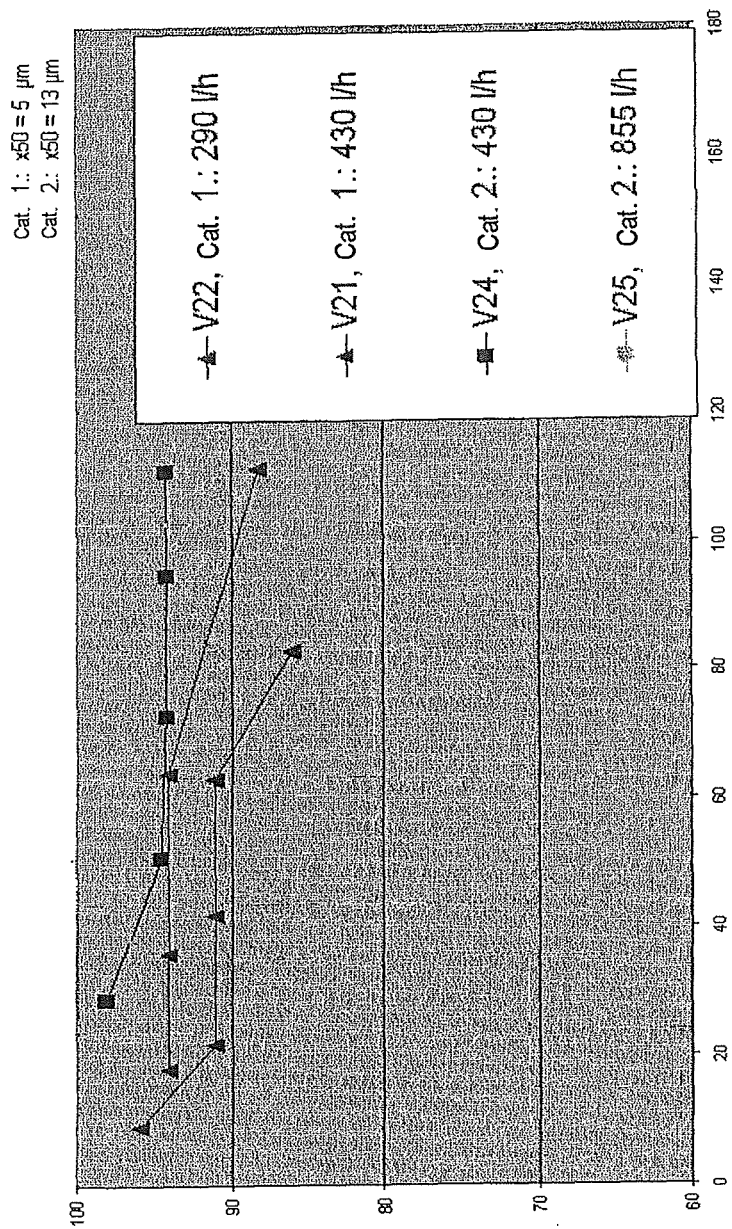
FIG. 5 shows the magnetic filter degree of deposition curves for example 1.

FIG. 4 schematically shows the experimental set-up used in the examples. In FIG. 4, the abbreviations have the following meanings:
R1 Temperature-controllable reservoir
F1 Magnetic filter
M Stirrer FIG. 5 shows the magnetic filter degree of deposition curves for example 1. The experimental conditions are: HMD, fine matrix, about 90 ppm by weight of catalyst.

Figure 6:
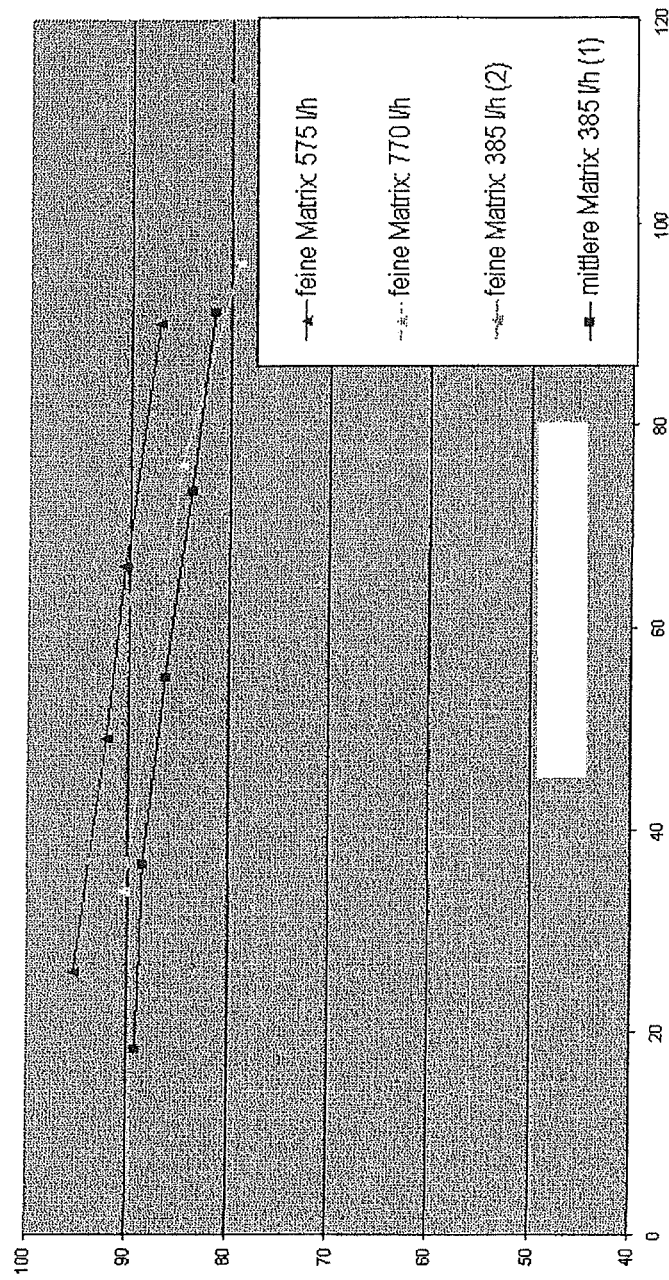
FIG. 6 shows the magnetic filter degree of deposition curves for example 2.

FIG. 6 shows the magnetic filter degree of deposition curves for example 2. The experimental conditions are: water, $x_{50}=3.4$ μm, about 130 ppm by weight of catalyst.

In FIGS. 5 and 6, the degree of deposition is in each case plotted on the y axis in % by weight and the suspension volume in l is in each case plotted on the x axis.

EXAMPLES

The present examples illustrate the present invention without constituting a restriction.

Example 1

Raney nickel-comprising crude HMD from an industrial plant for the low-pressure hydrogenation of ADN, specifically from the overflow of the first hydrocyclone, is used as starting material. The starting material comprises 90 ppm by weight of Raney nickel, determined by AAS (atomic absorption spectrometry) analysis. The average particle size of the Raney nickel is from 5 or 13 μm, determined by laser light scattering measurement (Master Sizer 2000, from Malvern).

The starting material is purified by means of a high-gradient magnetic filter (model HGF10) from Steiner.

FIG. 4 schematically shows the experimental set-up. The crude HMD is placed in a stirred, temperature-controllable 400 l reservoir (R1). The magnetic filter (F1) is located in a pumped circuit operated by means of a pump. Backflushing of the loaded filter is carried out by means of deionized water into a collection vessel. Appropriate instrumentation makes it possible to set the amounts in the pumped circuit, to measure the pressure drop in the filter and the amount of backflushing water and also the temperature of the plant. The following filter matrix is used in this filter.

Matrix (L×B×T): 20×80×100 mm
Matrix area: 1600 mm$^2$
Matrix mesh opening: 0.5 mm, 1.0 mm, 1.5 mm All experiments are carried out at 25° C. and a filter pressure of about 1 bar (absolute). However, the experimental results achieved are independent of the filtrate pressure. The filtrate pressure is limited only by the maximum permissible operating pressure of the filter housing (minus the differential pressure during filtration). The deposition performance is limited by the magnetic material properties of the filter matrix and of the iron circle of the high-gradient magnetic filter. For a good degree of separation, the operating temperature should therefore not be above 80° C. in the case of the materials used at present. When other materials whose magnetic materials properties are impaired only slightly, if at all, above 80° C. are used according to the invention, higher operating temperatures can be employed.

The magnetic flux density of the test filter is 0.3 T (25 mm pole spacing). The filter matrix is packed with wire mesh layers made of the material X6Cr17 (ferromagnetic stainless steel).

Experimental Results

A volume flow of from 0.290 to 0.855 m³/h of HMD comprising about 90 ppm by weight of catalyst particles is conveyed through the magnetic filter at a temperature of 25° C. and 1 bar (abs.). The residence time in the filter matrix is from 0.68 to 2 seconds.

The degree of deposition for a stream of 0.29 m³/h comprising catalyst particles having an average particle size of 5 µm is from 90 to 95%, corresponding to a residual amount of 4.5 ppm by weight (see FIG. 5).

The degrees of deposition are as expected better for the fine-structured filter matrix having a mesh opening of 0.5 mm (triangular symbols) than for the larger filter matrix having a mesh opening of 1.0 mm (square symbols). With increasing loading, the degree of deposition decreases due to the increasing weakening of the magnetic field gradient and impairment of the flow conditions in the filter matrix. Likewise, the degrees of deposition decrease with higher liquid throughput through the matrix (inflow velocity achieved of from 3.2 to 9.4 cm/s).

The degrees of deposition of the magnetic filter are determined by determining the particulate nickel concentration downstream of the filter (no dissolved nickel fraction in the HMD) with and without an applied magnetic field. This procedure ensures that exclusively the magnetic degree of deposition is taken into account. In addition, a long-term experiment carried out without a magnetic field shows that mechanical filtration in any case does not take place to a significant extent (stable exit concentration since there is no increase in the pressure drop).

The storage capacity of the filter matrix is, for the region of still moderate deteriorations in the degree of deposition, about 5 g of catalyst (coarser matrix) to about 7.5 g of catalyst (fine matrix) per 100 cm³ of matrix volume.

In all cases, the loaded matrix can be largely cleaned by means of a backflushing pulse with about 1 l of water per second (duration: 3 to 4 seconds). Repetitions of the backflushing operation give only a slight additional catalyst discharge. After the end of the experiments, no permanent increase in the basic pressure drop of the matrix can be observed.

Example 2

Milled Raney nickel ($x_{50}$=about 3.4 µm) suspended in water serves as starting material. Milling is carried out in a stirred mill.

The experimental apparatus corresponds to example 1.

Experimental Results

A volume flow of from 0.385 to 0.77 m³/h of aqueous suspension comprising about 130 ppm by weight of catalyst particles having an average particle size of 3.4 µm is conveyed through the magnetic filter at a temperature of 25° C. and 1 bar. The residence time in the filter matrix is from 0.75 to 1.5 seconds.

The degree of deposition for a stream of 0.385 m³/h is from 90 to 95%, corresponding to a residual amount of 6.5 ppm by weight. The degrees of deposition are as expected better for the finely structured filter matrix having a mesh opening of 0.5 mm (triangular symbols) than for the coarser filter matrix having a mesh opening of 1.0 (square symbols). The degree of deposition decreases with increasing loading, owing to the increasing weakening of the magnetic field gradients and the impairment of the flow conditions in the filter matrix. The degrees of deposition likewise decrease with higher liquid throughput through the matrix (inflow velocity achieved from 4.3 to 8.6 cm/s).

The degrees of deposition of the magnetic filter are again determined by determining the particulate nickel concentration downstream of the filter (no dissolved nickel fraction in the water) with and without an applied magnetic field.

In all cases, the loaded matrix could be largely cleaned by means of a backflushing pulse of about 1 l of water per second (duration: about 3 to 4 seconds). Repetitions of the backflushing operation give only a slight additional catalyst discharge.

The experiment shows, for the example of Raney nickel, that ferromagnetic catalyst particles can be separated off from aqueous suspensions or emulsions by means of magnetic filters.

Example 3

Example 3 shows that a significantly smaller amount of by-products is formed on thermal stressing of hexamethylenediamine (HMD) in the presence of a small amount according to the invention of catalyst (e.g. <5 ppm by weight) coming from the hydrogenation previously carried out, as occurs, for example, in a distillation column used for purifying the product, so that, firstly, the purity of the product and also the yield of desired product increases. HMD was stirred under nitrogen as inert gas in the presence of suspended Raney nickel. The concentration of tetrahydroazepine (THA)

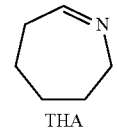

THA as by-product formed is determined by way of example after particular times. The by-product THA can generally only be separated off from hexamethylenediamine with a high outlay for distillation, see WO 01/66514, page, lines 31 to 39.

The amount of THA in pure HMD should not exceed 100 ppm (Ullmann's Encyclopedia of Industrial Chemistry, 6$^{th}$ completely revised edition, volume 16, page 435, column 1).

Example 3.1

Comparative Example

Pure HMD is stirred at 180° C. with 1% by weight, corresponding to 10 000 ppm by weight, of Raney Ni, at atmospheric pressure under nitrogen as protective gas.

| t (min) | c (THA) in % by weight |
|---------|------------------------|
| 0       | 0.05                   |
| 34      | 2.08                   |
| 82      | 3.35                   |
| 292     | 5.72                   |

This implies a rate of formation of THA of about 0.7% by weight/h

Example 3.2

Comparative Example

Pure HMD is stirred at 150° C. with 1% by weight, corresponding to 10 000 ppm by weight, of Raney Ni, at atmospheric pressure under nitrogen as protective gas.

| t (min) | c (THA) in % by weight |
|---|---|
| 0 | 0.14 |
| 8 | 0.42 |
| 75 | 1.69 |
| 221 | 2.26 |
| 363 | 4.19 |

Example 3.3

According to the Invention

Pure HMD is stirred at 200° C. without Raney Ni (i.e. <5 ppm by weight of Raney nickel), at atmospheric pressure under nitrogen as protective gas.

| t (min) | c (THA) in % by weight |
|---|---|
| 0 | 0.06 |
| 1440 | 0.10 |

Example 3.4

Comparative Example

Pure HMD is stirred at 180° C. with 65 weight-ppm Raney-Ni without pressure under nitrogen as inert gas.

| t (min) | c (THA) in % by weight |
|---|---|
| 0 | 0.06 |
| 10 | 0.15 |
| 60 | 0.40 |
| 180 | 0.60 |
| 420 | 1.14 |

This experiment shows that significant amounts of tetrahydroazepine (THA) are obtained even with a low concentration of Raney-Ni. The THA-concentration of HMD is obtained in all experiments of example 3 by gas chromatography.

Example 4

According to the Invention

Two back-flushable magnetic filters of type automag SKID AM12/SKID1 of Eclipse Magnetics ltd. which are arranged in parallel, were tested in an industrial facility for low pressure-hydrogenation of ADN. Therefore, the overflow stream of the first hydrocyclone (Raney-nickel comprising crude HMD) is fed into a container, wherein a part of the catalyst particles agglomerated. Out of this container, Raney-nickel comprising crude HMD was fed to each of the two magnetic filters 6 t/h (about 7.3 m$^3$/h) with 70 to 100° C. continuously. The retention time in the container having a volume of 55 m$^3$ was 3.5 h.

The feed of the container did comprise 30 to 60 ppm by weight Raney-nickel during the experiments, analyzed by AAS-(atom-adsorption spectrometry)-analysis. The Raney-nickel particle size in the feed to the container was about 5 or 13 µm.

The drain of the container did comprise about 30 to 60 ppm by weight Raney-nickel. The average particle size of the Raney-nickel in the drain of the container was 30 to 80 µm.

The drain of the container was purified from catalyst by a magnetic filter (type automag SKID AM12/SKID12, Eclipse Magnetics ltd.).

For cleaning, the magnetic filters were back-flushed with feed suspension each 12 to 24 hours. For this, the permanent magnets were lifted at the inside of the magnetizable metal tubes in the filters, and the valve for draining the solid was opened.

The results obtained are independent from the pressure of the filtrate. The pressure of the filtrate according to this example is only limited by the at most admissible operating pressure of the filter housing. The filtration efficiency according to this example is limited by the magnetic material properties of the filter built-in components and of the permanent magnets of the magnetic filter. According to this example, the separation efficiency is not decreased, although the temperature of the feed is lowered. Because the magnetic flux density, which acts onto the particles, increases at temperatures<70° C., the viscosity that increases at lower temperatures, which degrades the particle preparation a little bit, is compensated.

Other materials according to the present invention, of which magnetic material properties do not or only insignificantly worsen above 100° C., according to the present invention can also be operated at higher operating temperatures.

Experimental Results

A volume flow rate of about 7.3 m$^3$/h HMD with 30 to 60 ppm by weight catalyst particles is fed at a temperature of 70 to 100° C. and 1 to 5 bar (abs.) to a magnetic filter (automag SKID AF12/SKID1).

The separation efficiency for this stream of 7.3 m$^3$/h, containing catalyst particles having an average particle size of 30 to 80 µm, is about 75%, according to the remaining amount of 8 to 15 ppm by weight.

With increasing loading of the filter, the separation efficiency decreases, caused by increasing weakening of the magnetic field gradient and degradation of the streaming conditions in the filter. Further, the separation efficiency decreases with a higher feed stream to the filter. Vice versa, the separation efficiency increases at a reduced feed. Furthermore, with a lower feed, smaller catalyst particles can be separated.

The storage capacity of the magnetic filter (automag SKID AN12/SKID1) is as a function of particle size about 4 to 6 kg, 12 kg at most.

In all cases the loaded magnetic filters can be cleaned with a flushing stream. The efficiency of this back-flushing operation only gives a marginal additional catalyst discharge. After ending of the experiments, no enduring increased of the space pressure loss can be detected.

The invention claimed is:

1. A process comprising:
    (A) hydrogenating adiponitrile to hexamethylene diamine in the presence of at least one heterogeneous catalyst in a reaction mixture, wherein the at least one heterogeneous catalyst comprises a metal selected from the group consisting of Ni, Fe, Co, and mixtures thereof, and wherein the at least one heterogeneous catalyst has a particle size distribution of 0.1 to 5000 µm, and
    (B) removing the at least one heterogeneous catalyst by means of a magnetic filter or a wet drum separator, wherein the magnetic filter is a back flushable magnetic filter and the content of the at least one heterogeneous catalyst in the reaction mixture which is used in step (B) is from 5 to 10,000 ppm by weight based on the reaction mixture;
    wherein at least part of the at least one heterogeneous catalyst is separated off after step (A) and before step (B), and wherein the removal before step (B) is carried out by filtration, by cross flow filtration, by separation in the earth's gravitational field, by sieving, or a combination thereof.

2. The process according to claim 1, wherein the removal before step (B) is carried out using at least one hydrocyclone, at least one settling vessel, at least one clarification vessel and/or at least one plate separator.

3. The process according to claim 1, wherein the removal before step (B) is carried out using a clarification vessel/settling vessel.

4. The process according to claim 1, wherein the removal before step (B) is carried out using a clarification vessel/settling vessel and a hydrocyclone.

5. The process according to claim 1, wherein the content of the at least one heterogeneous catalyst in the reaction mixture which is used in step (B) of the process of the invention is from 10 to 1000 ppm by weight, based on the reaction mixture to be treated.

6. The process according to claim 1, wherein the content of the at least one heterogeneous catalyst in the reaction mixture which is used in step (B) of the process of the invention is from about 20 to 500 ppm by weight, based on the reaction mixture to be treated.

7. The process according to claim 1, wherein the at least one heterogeneous catalyst has a particle size distribution of 1 to 1,000 μm.

8. The process according to claim 1, wherein the at least one heterogeneous catalyst has a particle size distribution of 1 to 100 μm.

9. The process according to claim 1, wherein the at least one heterogeneous catalyst that is present in the reaction mixture according to step (A) is agglomerated.

10. The method according to claim 1, wherein step (A) is performed at a temperature from 100 to 200° C. a pressure of from 200 to 400 bar, in the presence of ammonia.

11. The method according to claim 1, wherein step (A) is performed at a temperature from 60 to 100° C., a pressure from 20 to 50 bar, and in the presence of alkali metal-modified Raney nickel.

* * * * *